(12) United States Patent
Kuwahara et al.

(10) Patent No.: US 6,252,003 B1
(45) Date of Patent: Jun. 26, 2001

(54) POLYMER EMULSION AND PROCESS FOR PRODUCING THE SAME

(75) Inventors: Kazuo Kuwahara; Yoshihiro Hasebe; Akira Akaogi; Tsuneo Yasumura, all of Wakayama; Toshie Takahashi, Tokyo; Osamu Tachizawa, Tokyo; Eiji Terada, Tokyo, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/463,415

(22) PCT Filed: Oct. 30, 1998

(86) PCT No.: PCT/JP98/04935
§ 371 Date: Feb. 3, 2000
§ 102(e) Date: Feb. 3, 2000

(87) PCT Pub. No.: WO99/62974
PCT Pub. Date: Dec. 9, 1999

(51) Int. Cl.$^7$ .......................................... C08F 4/00
(52) U.S. Cl. .............................................. 525/242
(58) Field of Search ............................. 525/242

(56) References Cited

U.S. PATENT DOCUMENTS

| | | | | |
|---|---|---|---|---|
| 5,271,934 | * | 12/1993 | Goldberg | 424/401 |
| 5,498,421 | * | 3/1996 | Grinstaff | 424/450 |
| 5,639,473 | * | 6/1997 | Grinstaff | 424/450 |
| 5,891,477 | * | 4/1999 | Lanza | 424/501 |

FOREIGN PATENT DOCUMENTS

| | | |
|---|---|---|
| 0 803 513 | 10/1997 | (EP) . |
| 59-30722 | 2/1984 | (JP) . |
| 59-30722 | 7/1984 | (JP) . |
| 62-62827 | 3/1987 | (JP) . |
| 62-70401 | 3/1987 | (JP) . |
| 62-79201 | 4/1987 | (JP) . |
| 63-17902 | 1/1988 | (JP) . |
| 63-20302 | 1/1988 | (JP) . |
| 63-210101 | 8/1988 | (JP) . |
| 3-134038 | 6/1991 | (JP) . |
| 7-242772 | 9/1995 | (JP) . |
| 7-316203 | 12/1995 | (JP) . |
| 9-2933 | 1/1997 | (JP) . |
| 9-3106 | 1/1997 | (JP) . |
| 10-101706 | 4/1998 | (JP) . |

* cited by examiner

Primary Examiner—Paul R. Michl
(74) Attorney, Agent, or Firm—Oblon, Spivak, McClelland, Maier & Neustadt, P.C.

(57) ABSTRACT

The present invention provides a polymer emulsion which contains polymer particles having an average particle size of not more than 30 μm and having core-parts and shell-parts; which is composed of chitosan (a) and a polymer (b) of organic acids having a reactive vinyl group or a salt thereof, as constituent component of shell-part, and composed of a polymer (c) of hydrophobic monomers, as constituent component of core-part. Further, the present invention provides a coloring agent particle comprising a polymer particle in the above-mentioned polymer emulsion; and wherein a coloring material (k) is present in the shell-part and/or core-part. Furthermore, the present invention provides a deodorizing fiber wherein a polymer particle in the above-mentioned polymer emulsion is present on the surface of the fiber.

9 Claims, No Drawings

POLYMER EMULSION AND PROCESS FOR PRODUCING THE SAME

TECHNICAL FIELD

The present invention relates to a polymer emulsion which is useful as a skin cosmetic, a hair cosmetic, a pharmaceutical, a fiber treating agent, a deodorant, an aromatizer, an additive to cement, a coating material, a bactericidal/bacteriostatic agent, an agricultural chemical, etc., to a process for preparing the same and to use of the same.

BACKGROUND ART

Chitosan is a basic polysaccharide obtained by deacetylation of chitin being present in carapace of crustacean animals such as crab and shrimp, treated with a concentrated alkali. However, because of strong hydrogen bond in molecules, chitosan itself is hardly soluble in a solvent other than an acidic aqueous solution and, even it is made into an aqueous solution, viscosity of the solution becomes extremely high whereby its handling is difficult. Therefore, in order to make chitosan into fine particles, a method where chitosan is dissolved in an acid and the resulting solution is gradually dropped into an alkaline coagulating solution as disclosed in JP-A 59-30722, JP-A 62-62827, JP-A 62-70401, JP-A 62-79201 etc., a method where a solution of chitosan or a dispersion of chitosan is mechanically treated as disclosed in JP-A 63-20302, JP-A 63-17902, JP-A 63-210101, etc., and the like are available. However, in all of those methods, only particles in a size of several tens $\mu$m to several hundreds $\mu$m or more are obtained and they are not dispersible in water.

Accordingly, an object of the present invention is to obtain a polymer emulsion where polymer particles of a small particle size containing chitosan are dispersed in water and also to provide use of the said polymer emulsion and of the said polymer particles therein.

DISCLOSURE OF THE INVENTION

The present invention provides a polymer emulsion comprising polymer particles having core-part and shell-part and having an average particle size of not more than 30 $\mu$m, wherein the shell-part is composed of chitosan (a) and a polymer (b) of an organic acid having a reactive vinyl group or a salt thereof as constituent components, and wherein the core-part is composed of a polymer (c) of a hydrophobic monomer as constituent component or is composed of a mixture of the polymer (c) of a hydrophobic monomer and a non-polymerizable hydrophobic substance (d) as constituent component; and provides a process for preparing the same.

The present invention provides a coloring agent particle comprising shell-part composed of a hydrophilic polymer as the constituent component and core-part composed of a hydrophobic polymer as the constituent component, and a coloring material (k) being present in the shell-part and/or the core-part; and provides a hair cosmetic comprising the same.

The present invention provides a deodorizing fiber having a deodorant comprising the following component (S) and the following component (b) on the surface of the fiber; and provides a process for preparing the same; component (S): a high molecular substance having an amino group, component (b): a polymer of an organic acid having a reactive vinyl group or a salt thereof.

Incidentally, in the present invention, the term "polymer particle" means a polymer microsphere.

The present invention relates to the above-mentioned polymer emulsion; to a process for preparing the said polymer emulsion; to a polymer particle obtained from the said polymer emulsion; to a coloring agent particle containing the said polymer particles and coloring material included therein; to a hair cosmetic containing the said coloring agent particle; to a hair cosmetic composition containing the said coloring agent particle and a medium such as water and a surfactant; to a fiber deodorant containing the said polymer particle; and to a deodorizing fiber where the said fiber deodorant is present on the surface of the fiber.

The present invention further relates to use of the said polymer particle as a resin for including the coloring material, as a resin for hair cosmetic, or as a deodorizing fiber.

MODE FOR CARRYING OUT THE INVENTION

[1] Process for Preparing the Polymer Emulsion

The polymer emulsion of the present invention can be prepared by the following preparing processes (1) and (2).

Preparing process (1): which comprises emulsifying and dispersing, in water, chitosan (a), an organic acid having a reactive vinyl group or a salt thereof (e), a hydrophobic monomer (f), an oil-soluble polymerization-initiator (g) and, if necessary, a non-polymerizable hydrophobic substance (d), to obtain liquid particles of monomers having an average particle size of not more than 10 $\mu$m and polymerizing the liquid particles, to form core-part and shell-part of the polymer particle.

Preparing process (2): which comprises adding a hydrophobic monomer (f) and, if necessary, a non-polymerizable hydrophobic substance (d) to polymer particles (i) being miscible with the hydrophobic monomer (f) and having an average particle size of not more than 10 $\mu$m, to swell the polymer particles (i), further adding thereto an aqueous solution of chitosan (a) and an organic acid having a reactive vinyl group or a salt thereof (e) and polymerizing the core-part and the shell-part in the swollen polymer particles thus obtained in the presence of an oil-soluble polymerization-initiator (g) and, if necessary, a water-soluble polymerization-initiator (h).

[Chitosan (a)]

The chitosan (a) used in the present invention is a deacetylated product of chitin having the structure of (1→4)-2-acetamido-2-deoxy-β-D-glucan and has the structure of (1→4) -2-amino-2-deoxy-β-D-glucan. In the present invention, it may be a chitosan derivative where a part of the deacetylated amino groups or a part of hydroxyl groups in the same molecule is chemically modified such as acylation, etherification, esterification and other reactions. Usually, in the naturally occurring chitin, a part of the acetamido group is an amino group which is not acetylated and, therefore, chitosan which is used in the present invention is that where the degree of deacetylation is 30% or more.

[Organic Acid Having a Reactive Vinyl Group or a Salt Thereof (e)]

The organic acid having a reactive vinyl group used in the present invention is a water-soluble organic acid which is able to dissolve chitosan to give an aqueous solution and which has one or more reactive vinyl groups and one or more acidic groups in its molecule. Its specific examples include an unsaturated carboxylic acid monomer such as acrylic acid, methacrylic acid, crotonic acid, itaconic acid and maleic acid; an unsaturated sulfonic acid monomer such as styrenesulfonic acid, 2-acrylamido-2-methylpropanesulfonic acid, 3-sulfopropyl (meth)acrylate, bis(3-sulfopropyl)itaconate and vinylsulfonic acid; and an unsaturated phosphate monomer such as vinyl phosphate, bis(methacrylyloxyethyl)phosphate, diphenyl-2-acryloyloxyethyl phosphate, diphenyl-2-methacryloyloxyethyl phosphate, dibutyl-2-acryloyloxyethyl phosphate, dibutyl-2-methacryloyloxyethyl phosphate and dioctyl-2-(meth)acryloyloxyethyl phosphate. One or more of them may be used. Among them, an unsaturated carboxylic acid monomer having a relatively low acidity is preferred and a methacrylic acid having a low acidity in a state of polymer is most preferred.

Examples of the salt of such an organic acid having a reactive vinyl group (e) are alkaline metal salt (such as Na and K salts) and ammonium salt.

It is also possible that, together with the vinyl monomer (e), various acids may be optionally mixed. Examples of the acid to be mixed in this case include an inorganic acid such as hydrochloric acid, sulfuric acid and phosphoric acid and an organic acid such as formic acid, acetic acid, lactic acid, citric acid, tartaric acid, succinic acid, malic acid, oxalic acid, glycolic acid, dichloro acid and trifluoroacetic acid.

[Hydrophobic Monomer (f)]

There is no particular limitation for the hydrophobic monomer (f) which is used in the present invention so far as it is copolymerizable with the above-mentioned organic acid having a reactive vinyl group or a salt thereof (e) and it is hydrophobic. Preferably, however, its solubility in 100 g of water at 20° C. is less than 0.1 g. Examples of such ahydrophobic monomer include styrene; divinylbenzene; a (meth)acrylate such as butyl (meth)acrylate, 2-ethylhexyl (meth)acrylate, cyclohexyl (meth)acrylate, decyl (meth)acrylate, lauryl (meth)acrylate, dodecenyl (meth)acrylate, myristyl (meth)acrylate, palmityl (meth)acrylate, hexadecenyl (meth)acrylate, stearyl (meth)acrylate, octadecenyl (meth)acrylate and behenyl (meth)acrylate; a fluorine monomer such as trifluoroethyl methacrylate; and a silicone monomer. One or more of these hydrophobic monomers may be used.

[Oil-soluble Polymerization-initiator (g)]

The oil-soluble polymerization-initiator (g) used in the present invention is that which initiates the addition polymerization of a monomer by radical decomposition in the presence of heat or a reducing substance. An oil-soluble peroxide, an azobis compound, etc. are commonly used. Specific examples include an organic peroxide such as lauroyl peroxide and benzoyl peroxide; and an azo compound such as 2,2'-azobisisobutyronitrile, 2,2'-azobis(2,4-dimethylvaleronitrile) and 2,2'-azobis(2-methylbutyronitrile). One or more of these polymerization initiators may be used.

[Water-soluble Polymerization-initiator (h)]

The water-soluble polymerization-initiator (h) used in the present invention is that which initiates the addition polymerization of a monomer by radical decomposition in the presence of heat or a reducing substance. A water-soluble peroxo disulfate, a peroxide, an azobis compound, etc. are commonly used. Specific examples include a peroxo disulfate such as potassium persulfate and ammonium persulfate; a peroxide such as hydrogen peroxide and t-butyl hydroperoxide; and an azo compound such as 2,2'-azobis-2-amidinopropane salt (V-50) and 4,4'-azobis-4-cyanopentanoic acid. If necessary, they may be combined with a reducing agent and used as an initiator of a redox type.

[Non-polymerizable Hydrophobic Substance (d)]

Examples of the non-polymerizable hydrophobic substance (d) used in the present invention include a wax, an oil, a perfume, a cool-feeling agent, a warm-feeling agent, a plasticizer and a chain-transfer agent. When a perfume, a cool-feeling agent or a warm-feeling agent is included in polymer particles in this case, it is possible to maintain aroma or pharmaceutical effect for long time. Examples of the wax include a natural wax such as a petroleum wax and an animal- or plant-derived wax; a processed natural wax such as a hydrogenated product of the above; and a synthetic wax such as Fischer-Tropsch wax and polyethylene wax.

Examples of the oil include a silicone oil such as dimethyl polysiloxane and methylphenyl polysiloxane; a hydrocarbon oil such as liquid paraffin, isoparaffin and squalane; an ester oil such as isopropyl myristate, cetyl octanoate, octyldodecyl myristate and diisopropyl myristate; a higher alcohol such as a linear or branched alkyl glyceryl ether, cetanol and stearyl alcohol; and a natural animal and plant oil such as olive oil, jojoba oil, camellia oil, cotton seed oil and mink oil.

Examples of the perfume used in the present invention include a terpene hydrocarbon such as α-pinene, β-pinene, myrcene, limonene and 1,8-cineole; and a hydrophobic perfume such as amyl acetate and amyl propionate (e.g., the perfumes mentioned at from line 19 of upper left column to line 13 of lower left column in page 3 of JP-A 3-32673). One or more of them may be used.

Examples of the cool-feeling agent used in the present invention include camphor, thymol, mint oil, peppermint oil, spearmint oil, 1-menthol and a menthol derivative. Examples of the warm-feeling agent include nonylic acid vanillylamide, capsaicin, zingerone, vanillyl butyl ether and a natural extract containing at least one of these members as the main ingredient such as red pepper extract (tincture), arnica tincture and ginger extract (tincture) as well as oleoresin having the same effect thereof. One or more of them may be used.

Examples of the plasticizer include an ester such as a phthalic acid diester, an adipic acid diester, a succinic acid diester, a sebacic acid diester, an abietate, a caprylate, a caproate, an acetate, an enanthate, a myristate and a citrate; a benzoate such as sucrose benzoate; a phosphate such as tricresyl phosphate; and diethylbenzene.

[Polymer Particle (i)]

There is no particular limitation for the polymer particle (i) which is used in the present invention and which is miscible with hydrophobic monomer (f) so far as they are the polymer particles having an average particle size of not more than 10 μm, preferably 0.01–10 μm. Examples of the applicable ones include an anionic polymer emulsion, a cationic polymer emulsion, a nonionic polymer emulsion, polymer fine particles and microgel.

[Process for Preparing the Polymer Emulsion (1)]

In this preparing process, there is no particular limitation for the compounding ratio of chitosan (a) to the organic acid having a reactive vinyl group or a salt thereof (e) so far as the acid having no double bond is used therewith. On the other hand, when an acid having no double bond is not used together, it is preferred to use an organic acid having a reactive vinyl group or a salt thereof (e) in an amount of 0.75 to 10 moles calculated per a monosaccharide unit of chitosan. When it is less than 0.75 mole, there is a tendency that chitosan is not completely dissolved in water.

It is preferred that the compounding ratio of chitosan (a) to the hydrophobic monomer (f) is 1–5000 parts by weight, more preferably 2–300 parts by weight, of chitosan (a) to 100 parts by weight of the hydrophobic monomer (f). When the amount of chitosan (a) to 100 parts by weight of the hydrophobic monomer (f) is less than 1 part by weight, there is a tendency that the performance of chitosan is not fully achieved; while, when it is more than 5000 parts by weight, there is a tendency that the stability of the polymer emulsion is deteriorated.

In this preparing process, it is preferred to use the oil-soluble polymerization-initiator (g) within the range of 0.05–10.0 parts by weight to 100 parts by weight of the hydrophobic monomer (f).

The polymerization in this preparing process may be carried out either in the presence of or in the absence of a surfactant. Examples of the surfactant to be used include a common anionic, cationic, nonionic and amphoteric surfactant.

Examples of the anionic surfactant include dodecyl sulfate, dodecyl benzenesulfonate and sulfate of polyoxyethylene nonylphenyl ether.

Examples of the nonionic surfactant include polyoxyethylene alkyl ether, polyoxyethylene alkyl phenyl ether and polyoxyethylene-polyoxypropylene block copolymer.

Examples of the cationic surfactant include octadecyl trimethylammonium chloride.

Examples of the amphoteric surfactant include alkyldimethylaminoacetyl betaine and 2-alkyl-N-carboxy-N-hydroxyimidazolinium betaine.

However, since amphoteric ion is present in the polymer particle, nonionic surfactant is preferred when stability, etc. of the particle is taken into consideration. Although there is no particular limitation for the amount of the surfactant, it is preferred to use the surfactant within the range of 0.1–20 parts by weight to 100 parts by weight of the hydrophobic monomer (f).

In this preparing process, it is also possible to use a water-soluble high molecular compound as an emulsifier. Examples of the water-soluble high molecular compound include polyvinyl alcohol and a derivative thereof, starch and a derivative thereof and a derivative of cellulose.

There may be used one or more of these surfactants and water-soluble high molecular compounds.

In this preparing process, it is also possible in the emulsification of the hydrophobic monomer (f) to use a non-polymerizable hydrophobic substance (d) by mixing it with a hydrophobic monomer (f). In this case, the amount of the non-polymerizable hydrophobic substance (d) to the hydrophobic monomer (f) forming the core-part is desirably 0–90% by weight and preferably desirably 1–50% by weight.

It is further possible in the emulsification of the hydrophobic monomer (f) to use a hydrophilic monomer (j) by mixing it with a hydrophobic monomer (f). In this case, the amount of the hydrophilic monomer (j) to the hydrophobic monomer (f) forming the core-part is desirably 0–50% by weight and preferably desirably 0–20% by weight. When the amount of the hydrophilic monomer (j) is more than 50% by weight, an emulsion polymerization vigorously takes place at the same time whereby synthesis of an emulsion having a good stability is difficult.

In this case, although there is no particular limitation for the hydrophilic monomer (j) used therefor so far as it is hydrophilic and is copolymerizable with the above-mentioned organic acid having a reactive vinyl group or a salt thereof (e) and hydrophobic monomer (f), the preferred one is that where its solubility in 100 g of water at 20° C. is 0.1 g or more. Examples of such a hydrophilic monomer include an organic acid having a reactive vinyl group or a salt thereof (examples of the salt may be alkaline metal salt such as sodium and potassium and ammonium salt) including an unsaturated carboxylic acid monomer such as methyl (meth)acrylate, hydroxyethyl (meth)acrylate, hydroxypropyl (meth)acrylate, polyethylene glycol mono(meth)acrylate, glycidyl (meth)acrylate, (meth)acrylamide, N,N-dimethyl (meth)acrylamide, diacetone (meth)acrylamide, vinyl acetate, etc., acrylic acid, itaconic acid and maleic acid; an unsaturated sulfonic acid monomer such as styrenesulfonic acid, 2-acrylamido-2-methylpropanesulfonic acid and vinylsulfonic acid; and an unsaturated phosphate monomer such as vinyl phosphate and bis(methacryloxyethyl)phosphate. One or more of these hydrophilic monomers may be used.

In this preparing process, the above-mentioned chitosan (a), organic acid having a reactive vinyl group of a salt thereof (e), hydrophobic monomer (f), oil-soluble polymerization-initiator (g) and, if necessary, non-polymerizable hydrophobic substance (d) are mixed with water and the resultant mixture is emulsified by means of a mechanical stirring using an emulsifying device whereupon an O/W (oil-in-water) emulsion containing monomer liquid particles of an average particle size of not more than 10 μm is prepared. When the average particle size of the monomer liquid particles is more than 10 μm in this case, an average particle size of the polymer particles in the obtainable polymer emulsion becomes more than 30 μm and that is not preferred.

Examples of the emulsifying device used here include an ultrasonic homogenizer, a homo-mixer, a milder, an attriter, a (super) high pressure homogenizer, a nanomizer system and a membrane emulsifying device. With regard to the concentration of solid content during the emulsification, it is desirable to select from the range of 1–60% by weight.

In this preparing process, polymerization is carried out by warming the O/W emulsion prepared as mentioned above. Although the temperature for polymerization varies depending upon the type of the initiator, it is appropriately within the range of about 40–90° C. Although the time for polymerization varies depending upon the monomer, the type of the polymerization initiator and reaction temperature, 1–24 hours is usually appropriate. It is also possible that, in order to polymerize the organic acid having a reactive vinyl group or a salt thereof (e) in the shell-part of the monomer oil-particles, the water-soluble polymerization initiator (h) is added during the polymerization of or after completion of the polymerization of the core-part.

Its amount is preferably within the range of 0.05–20% by weight to the organic acid or the salt thereof (e). Incidentally, it is also possible to further add chitosan (a) and the organic acid having a reactive vinyl group or the salt thereof (e) for increasing an amount of the chitosan content of the polymer particles.

[Process for Preparing the Polymer Emulsion (2)]

This preparing process is that the polymer particles (i) having an average particle size of not more than 10 μm and being miscible with the hydrophobic monomer (f) are swollen with the hydrophobic monomer (f) or that the polymer particles (i) having an average particle size of not more than 10 μm are swollen with the non-polymerizable hydrophobic substance (d) and the hydrophobic monomer (f) so that chitosan (a) and the organic acid having a reactive vinyl group or a salt thereof (e) are made into protective colloid whereby a polymerization is carried out in the presence of a polymerization initiator. When the average particle size of the polymer particles (i) is more than 10 μm in this case, an average particle size of the polymer particles in the obtainable polymer emulsion exceeds 30 μm and that is not preferred.

In this preparing process, amount of the hydrophobic monomer (f) to the polymer particles (i) is preferably 5–20000% by weight and more preferably 10–1000% by weight calculated on a basis of a solid content. When the amount of the hydrophobic monomer is less than 5% by weigh, there is a tendency that bond of core-part with shell-part becomes insufficient; while, when it is more than 20000% by weight, the stability becomes insufficient.

Examples of the process for swelling the polymer particles (i) by the hydrophobic monomer (f) or, in some cases, by the non-polymerizable hydrophobic substance (d) and the hydrophobic substance (f) include a method where the hydrophobic monomer (f) is added to the polymer particles (i) and a method where the hydrophobic monomer (f) is emulsified or the hydrophobic monomer (f) and the water-soluble organic solvent are emulsified using a surfactant and then the resultant emulsion is added to the polymer particles (i) dispersed in water. In this case, the non-polymerizable hydrophobic substance (d) may be added together with the hydrophobic monomer (f) and the amount of the non-polymerizable hydrophobic substance (d) is desirably 0–90% by weight and preferably desirably 1–50% by weight to the hydrophobic monomer.

When the polymer particles which are swollen by the hydrophobic monomer (f) or by the non-polymerizable hydrophobic substance (d) and the hydrophobic monomer (f) are dispersed in water, a surfactant may be used. The surfactant which is used here may be any type of anionic, cationic and nonionic surfactants. Its amount used to the polymer particles is desirably 1–50% by weight.

In this preparing process, the polymer particles (i) are swollen with the hydrophobic monomer (f) or with the non-polymerizable hydrophobic substance (d) and the hydrophobic monomer (f) as mentioned above, then an aqueous solution of chitosan (a) and the organic acid having a reactive vinyl group or a salt thereof (e) is further added thereto and, with regard to the swollen polymer particles thus obtained, core-parts and shell-parts are polymerized in the presence of the oil-soluble polymerization initiator (g) and, if necessary, the water-soluble polymerization initiator (h).

In this preparing process, the compounding amounts of chitosan (a), the organic acid having a reactive vinyl group or a salt thereof (e) and the polymerization initiator(s) are the about same as those in the case of the above-mentioned preparing process (1)

The chitosan-containing polymer emulsion, which is obtained by the above preparing processes (1) and (2), may be neutralized using a base.

Examples of the base used here include ammonia, methylamine, ethylamine, propylamine, butylamine, isobutylamine, hexylamine, octylamine, amino-modified silicone, ethylenediamine, propylenediamine, butylenediamine, sodium hydroxide, potassium hydroxide, calcium hydroxide, sodium carbonate, sodium alkoxide and potassium alkoxide.

The adding amount of the base to the organic acid polymer in the emulsion is preferably 0.1–2.0 % by mole and particularly preferably 0.6–1.2 % by mole.

[Polymer Particles in the Polymer Emulsion]

The polymer particles in the polymer emulsion obtained in the present invention have an average particle size of not more than 30 μm, preferably 0.01–30 μm and more preferably 0.05–10 μm. In case that the average particle size is more than 30 μm, stability of the emulsion upon preservation is poor.

Incidentally, in the present invention, an average particle size of the polymer particles was determined by a measurement using a particle size distribution measuring device of a laser diffraction type (LA-910 manufactured by HORIBA).

The polymer particles in the polymer emulsion obtained by the present invention have core-part and shell-part and, in the shell-part, chitosan (a) and polymer (b) of the organic acid having a reactive vinyl group or a salt thereof are the constituting components while, in the core-part, polymer (c) of the hydrophobic monomer is the constituting component.

The polymer emulsion and the polymer particles in the present invention as above can be used in coloring agent particles and hair cosmetics containing the same and also in deodorizing fiber.

[2] Coloring Agent Particles and Hair Cosmetics

When the polymer emulsion of the present invention is used, coloring agent particles having the following effect and a hair cosmetic containing the same can be obtained.

Thus, the present invention provides coloring agent particle which is composed of shell-part where the hydrophilic polymer is the constituting component and of core-part where the hydrophobic polymer is the constituting component and the coloring material (k) is present in the said shell-part and/or core-part.

In case that such coloring agent particles are used in a hair cosmetic, the coloring agent particles cover the hair and are fixed on the hair when the hair cosmetic is applied on the surface of the hair by hand. In addition, even after rising, the coloring material can be adsorbed with the hair in large amount and, accordingly, a high coloring effect can be obtained by a simple operation with very little coloring of head skin and hand which are more hydrophilic.

Examples of the hydrophilic monomer (j) which constitutes the hydrophilic polymer of the shell-parts are the same as those which are exemplified above. Examples of the hydrophilic polymer include chitosan.

Among these members, chitosan (a) and the polymer (b) of the organic acid having a reactive vinyl group or a salt thereof are preferably used.

The organic acid having a reactive vinyl group or the salt thereof (e) is a water-soluble organic acid having one or more reactive vinyl groups and one or more acidic groups in a molecule and being able to dissolve chitosan (a) to give an aqueous solution and, among the above-mentioned ones, an unsaturated carboxylic acid monomer having a relatively low acidity is preferred and methacrylic acid giving a polymer of low acidity is most preferred.

Examples of the hydrophobic monomer (f) constituting the hydrophobic polymer of the core-part are the same as those exemplified above.

Examples of the coloring material (k) include a water insoluble pigment, an oil-soluble dye, a vat dye and a lake dye. Examples of the pigment include an inorganic pigment such as carbon black, talc, kaolin, mica, mica titanium, red iron oxide, magnesium silicate and titanium oxide; and an organic pigment such as Red No. 202, Red No. 204, Red No. 205, Red No. 206, Red No. 219, Red No. 228, Red No. 404, Yellow No. 205, Yellow No. 401, Orange No. 401 and Blue No. 404. Examples of the oil-soluble dye include Red No. 505, Red No. 501, Red No. 225, Yellow No. 404, Yellow No.405, Yellow No. 204, Orange No. 403, Blue No. 403, Green No. 202 and Purple No. 201. Examples of the vat dyes are Red No. 226, Blue No. 204 and Blue No. 201. Examples of the lake dye include various acidic dyes which are laked with aluminum or barium.

One of these coloring materials (k) may be used solely or two or more of them may be used jointly and it is preferred that the coloring materials (k) is preferably contained in an amount of 1–50% by weight, and particularly 2–30% by weight, in the coloring agent particles.

Incidentally, the coloring material (k) may be present in any area of the coloring agent particles.

When the coloring material (k) and titanium oxide are made co-present in the same particle, dyeing of the coloring material (k) can be promoted. In this case, it is preferred to use titanium oxide in an amount of 0.1–40% by weight, particularly 1–30% by weight, to the coloring material.

The coloring agent particles of the present invention are prepared, for example, in such a manner that the core-part is formed by polymerizing the hydrophobic monomer (f), using the hydrophobic monomer (f), the hydrophilic monomer (j) and the coloring material, in the presence of the oil-soluble polymerization initiator (g) and then the shell-part is formed by polymerizing the hydrophilic monomer (j) in the presence of the hydrophilic monomer (j) in the presence of the water-soluble polymerization initiator (h). To be more specific, the said particles can be prepared by a method wherein monomer liquid particles having an average particle size of not more than 10 $\mu$m obtained by an emulsion dispersion of the hydrophilic monomer (j), the hydrophobic monomer (f), the coloring material (k), the oil-soluble polymerization initiator (g) and, if necessary, the non-polymerizable hydrophobic substance (d) is dispersed in water in an emulsion form and then polymerization is carried out after addition of the water-soluble polymerization initiator (h) to form the core-part and the shell-part of the polymer particle; alternatively a method wherein the polymer particles (i) having an average particle size of not more than 10 $\mu$m and being miscible with the hydrophobic monomer (f) are swollen by adding the hydrophobic monomer (f), the coloring material (k) and, if necessary, the non-polymerizable hydrophobic substance (d) thereto, then an aqueous solution of the hydrophilic monomer (j) is added and core-part and shell-part are polymerized in the swollen polymer particles thus obtained in the presence of the oil-soluble polymerization initiator (g) and, if necessary, the water-soluble polymerization initiator (h); etc.

Among these members, when the shell-part has chitosan (a) and the polymer (b) of the organic acid having a reactive vinyl group or the salt thereof as the constituting components thereof, it can be prepared, for example, by the above-mentioned preparing process (1) or (2).

That is, the coloring material (k) is made present together with the hydrophobic monomer (f) in the preparing process (1) or (2).

The coloring agent particles in the polymer emulsion obtained, as such process, has an average particle size of preferably not more than 30 $\mu$m, more preferably 0.01–30 $\mu$m, particularly preferably 0.1–10 $\mu$m and still more preferably 0.5–10 $\mu$m.

Incidentally, in the present invention, the average particle size of the coloring agent particles was measured by a particle size distribution measuring device of a laser diffraction type (LA-910 manufactured by HORIBA).

In the present invention, the obtained polymer emulsion of the coloring agent particles may be used as it is.

The hair cosmetic of the present invention contains such coloring agent particles and water. With regard to the coloring agent particles, one type may be used solely or two or more types may be compounded jointly and it is preferred in terms of coloration of hair and feel in actual use that their compounding amount in the total composition is 0.05–40% by weight, particularly 0.1–30% by weight and still particularly 0.5–10% by weight.

In order to obtain hair cosmetic having optional color, in the present invention, two or more coloring agent particles are compounded or two or more cosmetics containing two or more coloring agent particles may be mixed and used.

In the hair cosmetic of the present invention, the following components which are commonly used in a conventional hair cosmetic may be further and appropriately compounded therewith or included in the particles besides the above-mentioned components if the effect of the present invention is not deteriorated. For example, they may be a surfactant such as a cationic surfactant, an anionic surfactant, a non-ionic surfactant and an amphoteric surfactant; a higher alcohol; a hydrocarbon such as liquid paraffin and vaseline; a derivative of lanolin such as liquid lanolin and a lanolin fatty acid; a phospholipid such as lecithin; a sterol such as cholesterol and a derivative thereof; a peptide obtained by decomposition of collagen; a perfluoro polyether; a fat/oil such as an ester of a higher alcohol and a higher fatty acid and a higher fatty acid; an animal and plant fat/oil such as mink oil and olive oil; a pharmaceutical such as an anti-dandruff agent, a germicide and a vitamin; a polyol such as glycerol and propylene glycol; a preservative such as paraben; a thickener such as a water-soluble high molecular compound; a coloring agent such as a dye and a pigment; an ultraviolet absorber; a plant extract; an astringent; a perfume; a coloring matter; etc.

The hair cosmetic of the present invention may be prepared by a common method and there is no particular limitation for its prepared form. For example, a hair rinse, a hair treatment, a hair conditioner, a hair pack, a hair lotion and a hair shampoo may be made up. Particularly, the form of a hair rinse, a hair treatment, a hair conditioner, a hair pack, etc., which are applied to hair and then rinsed out, are suitable.

The coloring agent particle of the present invention is able to selectively color the hydrophobic surface.

In addition, the hair cosmetic of the present invention exhibits excellent stability, selectively colors the hydrophobic surface (hair), gives little coloration to the hydrophilic surface (skin), obtains a high coloring effect by a single operation in a simple method, do not damage the hair and shows an excellent feel in actual use.

[3] Deodorizing Fiber

When the polymer emulsion and the polymer particles of the present invention are used, color of the fiber is not deteriorated, an instant deodorizing effect is achieved. Moreover, a deodorizing fiber, which is excellent in lasting, can be obtained.

That is, the present invention provides a deodorizing fiber where the deodorant comprising the following component (S) and the following component (b) is present on the surface of fiber and also provides a process for preparing the same.

Component (S): a high molecular substance having an amino group

Component (b) polymer of an organic acid having a reactive vinyl group or a salt thereof The deodorant of the present invention is present on the fiber surface either continuously or discontinuously and, for example, it may be either in the form of particles or film. In the case of particles, an average particle size is preferably 0.01–100 $\mu$m and more preferably 0.01–50 $\mu$m. The average particle size can be confirmed by means of an electron microscope. In the case of film, the film may be a continuous one or it may have a discontinuous part.

Examples of the component (S) of the deodorant include polygalactosamine, chitosan (a) (polyglucosamine), chitin, polyethyeneimine and polyaniline. In view of the stability as a polymer and also of the low smell of itself thereto, chitosan (a) is particularly preferred. A weight average molecular weight of this component (b) is preferably within a range of 5,000–500,000.

The component (b) of the deodorant is a polymer of a vinyl monomer (e) and, among them, a polycarboxylic acid such as polyacrylic acid, polymethacrylic acid, polycrotonic acid, polyitaconic acid and polymaleic acid are used preferably. Polyacrylic acid, polymethacrylic acid, and particularly polymethacrylic acid having the lowest acidity and being easily salt-exchangeable with an other acidic smell substance are preferred.

The component (b) may be a copolymer of a monomer of an amide type such as acrylamide, methyl acrylamide, dimethyl acrylamide, diethyl acrylamide and 3-acrylamido-N,N-dimethylpropylamine having an interaction with an electron donor (such as a ketone) which is a bad smell component.

Further, a part or all of the acid groups of the component (b) may be in the form of salt and the examples thereof include a salt with an alkaline metal such as lithium, sodium and potassium; a salt with an alkaline earth metal such as calcium; a salt with an organic amine such as methylamine, ethylamine and butylamine; and a salt with amino acid such as alanine and glycine. In view of low cost and low smell, salt with an alkaline metal such as sodium and potassium is preferred. Furthermore, a part of the acid groups of the component (b) may have been esterified.

A weight average molecular weight of the component (b) is preferably within a range of 5,000–500,000.

In the deodorant, the component (S) and the component (b) may be in the form of mixture or complex. When the component (S) and the component (b) are present as complex, it can be confirmed by the fact that, upon observation of the deodorant pieces under an electron microscope (of 10,000 magnifications), both high molecular substances of the component (S) and the component (b) are present within a range of a square of 1 $\mu$m. When the component (S) and the component (b) do not satisfy the above condition, the component (S) and the component (b) form mixture.

In the present invention, it is preferred that the component (S) and the component (b) of the deodorant are present in the form of complex on the fiber surface in view of the effect that the deodorizing effect is both instant and lasting.

In any of the cases where the component (S) and the component (b) are present in the form of mixture and complex, the ratio of the component (S) to the component (b) (by weight) is preferably from 0.5/99.5 to 99.5/0.5 and more preferably from 20/80 to 75/25. When the ratio is within such a range, the excellent deodorizing effect which is desirable in the present invention is achieved.

The deodorizing fiber of the present invention may, for example, be prepared by the following preparing process (3) or (4).

Preparing process (3): which comprises bringing particles comprising the component (S) and the component (b) (hereinafter, referred to as "deodorant particles") into contact with a fiber or bringing a polymer emulsion of the particles or an organic dispersion of the particles (hereinafter, referred to as "deodorant particles dispersion") into the contact with a fiber, to have the deodorant in the form of particle comprising the component (S) and the component (b) on the surface of the fiber.

In carrying out the above process, a binder may be or may not be used. However, in view of resistance to laundry, use of a binder is preferred. Examples of the binder include a silicone type, an acrylic type, a urethane type and a vinyl acetate type. In this case, besides the binder, the other substance such as a softener, an antibacterial agent, a fluorescent dye, a shrink preventing agent such as glyoxal and a fixing agent, may be used jointly depending upon the object.

Methods for bringing the deodorant particle dispersion into contact with fiber commonly include a pad dry method using a mangle or a drier and an immersion method using an wince, a cheese a dyeing machine or a jet dyeing machine. However, a spraying method, a coating method and a textile printing method are available as well and, for a rayon and acrylic fiber, a kneading method is also possible.

When the deodorant particle dispersion is brought into contact with fiber and is adhered on the fiber surface, examples of the method therefor include a method where fiber is dipped in the dispersion followed by drying and a method where the dispersion is sprayed onto the fiber followed by drying.

When a deodorant particle dispersion is used, water and/or an organic solvent may be used as a dispersion medium. In this case, an organic solvent such as alcohol such as methanol, ethanol, propanol, isopropanol, butanol, hexanol, heptanol and octanol; such as a polar solvent such as acetone, acetonitrile, tetrahydrofuran, dioxane and ethyl acetate; such as a nonpolar solvent such as cyclohexane, hexane, heptane and octane are used preferably. Such a solvent may also be used by mixing with water in optional ratio.

In the deodorant particle dispersion, the average particle size of the deodorant particles is preferably 0.01–100 $\mu$m, more preferably 0.01–50 $\mu$m and particularly preferably 0.1–10 $\mu$m. The average particle size can be measured by a particle size measuring device of a laser diffraction type (LA-910).

Here, the deodorant particle dispersion and the deodorant particles are obtained in accordance with the above-mentioned preparing process (1) or (2). Thus, in place of chitosan (a) in the process, the above-mentioned deodorant component (S) is ample to use.

The deodorant particle dispersion prepared as such may be used as it is. Alternatively, this dispersion is mixed with a hydrophobic organic solvent to precipitate the deodorant particles and the resulting deodorant particles may be used.

Preparing process (4): which comprises mixing the component (S) with an organic acid having a reactive vinyl group or a salt thereof (e) and polymerizing the monomer (e) on the surface of the fiber, to have a deodorant in the form of film comprising the component (S) and the component (b) on the surface of the fiber.

A fiber is dipped in an aqueous solution of the starting monomer of the component (S) and the component (b) and squeezed with a mangle. And then polymerization reaction is carried out preferably at 60–90° C. and more preferably at 70–80° C. for five hours. After this reaction, the product is dried to be able to obtain a deodorizing fiber.

Examples of the fiber used in the present invention include a natural fiber such as cotton and linen; a regenerated fiber such as rayon, cupra and tencel; a semi-synthetic fiber such as acetate, diacetate and triacetate; and a synthetic fiber such as polyester, nylon, acrylic fiber, vinylon, polypropylene and polyurethane.

The present invention may be used in various modes of fiber such as staple fiber, yarn, nonwoven fabric, knitted cloth and woven cloth.

In the deodorizing fiber of the present invention, it is preferred that the deodorant is contained in an amount of 0.01–10.0% by weight in the deodorizing fiber.

In accordance with the present invention, it is possible to obtain a deodorizing fiber having excellent instant and lasting deodorant effect.

EXAMPLES

Example 1

To 2.5 g of commercially available chitosan (SK-10 manufactured by Koyo Chemical Co., degree of deacetylation: 85–88%, weight average molecular weight: 130000) were added 45 g of water, then 1.0 g of methacrylic acid (equimolar amount to the monosaccharide unit of chitosan) was added thereto and the resultant mixture was dissolved with stirring at 60° C. to prepare an aqueous solution of chitosan/methacrylic acid.

Then 50 g of stearyl methacrylate and 0.5 g of lauroyl peroxide were placed in a glass beaker to dissolve. 500 g of deionized water, 5 g of EMULGEN 420 (nonionic surfactant manufactured by Kao Corp.) and 50 g of the previously prepared aqueous solution of chitosan/methacrylic acid were added thereto and the resultant mixture was treated by an ultrasonic homogenizer (manufactured by Nippon Seiki Co. Ltd.) with stirring for 30 minutes to prepare an emulsion having the average particle size of 1.12 $\mu$m. This emulsion was transferred to a reactor made of glass equipped with a stirrer, a cooler and a nitrogen-introducing pipe. The inner air of the reactor was substituted with nitrogen and the inner of that temperature was made 75° C. by heating with stirring. Polymerization was carried out for 2 hours with stirring, then 0.1 g of ammonium persulfate dissolved in 10 g of water was added and the reaction was further carried out for 2 hours to obtain a polymer emulsion.

The obtained polymer emulsion was freeze-dried and observed by means of SEM (an observation was carried out after that gold was vapor-deposited onto the dried sample; SUPER SCAN-220 (registered trademark) manufactured by Shimadzu) and TEM (dried sample was subjected to a negative staining and a cross section was cut out by a microtome and subjected to a TEM observation; JEM 2000FX (registered trademark) manufactured by Nippon Denshi). Accordingly, it was confirmed that the polymer particles were spherical and in the structure of a core-shell type where the shell-part was a layer derived from hydrophilic chitosan while the core-part was composed of poly(stearyl methacrylate).

It was also confirmed that the polymer particles were in the same structure in the following Examples 2, 4–5 and 8–10 as well.

Example 2

The same operation as in Example 1 was carried out except that 25 g of stearyl methacrylate and 25 g of HNP-9 (paraffin wax manufactured by Nippon Seiro) were melted and mixed instead of 50 g of stearyl methacrylate whereby a polymer emulsion was obtained.

Example 3

The same operation as in Example 1 was carried out except that 50 g of lauryl methacrylate were used instead of 50 g of stearyl methacrylate whereby a polymer emulsion was obtained.

It was confirmed by the same method as in Example 1 that the resulting polymer particles were spherical and in the structure of a core-shell type where the shell-part was a layer derived from hydrophilic chitosan while the core-part was composed of poly(lauryl methacrylate)

Example 4

50 g of stearyl methacrylate and 0.5 g of lauryl peroxide were placed and dissolved in a beaker and mixed. And then, 50 g of an aqueous solution of chitosan/methacrylic acid prepared by the same manner as in Example 1 and 500 g of deionized water were mixed and the resultant mixture was treated by an ultrasonic homogenizer with stirring for 30 minutes whereupon a monomer emulsion was prepared. This monomer emulsion was heated at 75° C. of the inner temperature using the same reactor as in Example 1. Polymerization was carried out for 2 hours with stirring, then 0.1 g of ammonium persulfate dissolved in 10 g of water was added thereto and the reaction was further carried out for 2 hours to obtain a polymer emulsion.

Example 5

The same operation as in Example 1 was carried out using 2.0 g of methacrylic acid (2.0-valent moles to a chitosan unit) and 1.0 g of N,N-dimethylacrylamide instead of 1.0 g of methacrylic acid whereby a polymer emulsion was obtained.

Example 6

Into a reactor made of glass were charged 50 g of polystyrene latex (average particle size: 1.51 $\mu$m, solid content: 20%) obtained by a soap-free polymerization and were heated up to 40° C. of temperature.

Then 50 g of n-butyl methacrylate, 5 g of EMULGEN 420, 0.5 g of lauroyl peroxide and 200 g of deionized water were placed in a beaker and treated by an ultrasonic homogenizer for 30 minutes to obtain an emulsion having an average particle size of 0.58 $\mu$m. This emulsion was mixed with the above polystyrene latex and stirred at 40° C. for 90 minutes. After that, an aqueous solution of chitosan/methacrylic acid prepared by the same manner as in Example 1 was added and heated to make the inner temperature of 75° C. Polymerization was carried out with stirring for 2 hours, then 0.1 g of ammonium persulfate dissolved in 10 g of water was added and the reaction was further carried out for 2 hours whereby a polymer emulsion was obtained.

It was confirmed by the same method as in Example 1 that the resulting polymer particles were spherical and in the structure of a core-shell type where the shell-part was a layer derived from hydrophilic chitosan while the core-part was composed of a mixture of poly(n-butyl methacrylate) and polystyrene.

Example 7

In Example 6, the same operation as in Example 6 was carried out using 50 g of t-butyl methacrylate and 5 g of diisobutyl adipate instead of 50 g of n-butyl methacrylate to obtain a polymer emulsion.

It was confirmed by the same method as in Example 1 that the resulting polymer particles were spherical and in the structure of a core-shell type where the shell-part was a layer derived from hydrophilic chitosan while the core-part was composed of a mixture of poly(t-butyl methacrylate) and polystyrene.

Example 8

Into a beaker were placed 50 g of stearyl methacrylate, 10 g of limonene and 0.5 g of lauroyl peroxide to dissolve. And then, 50 g of an aqueous solution of chitosan/methacrylic acid prepared by the same manner as in Example 1 and 500 g of deionized water were mixed therewith and the resultant mixture was treated by an ultrasonic homogenizer with stirring for 30 minutes whereby a monomer emulsion was prepared. This monomer emulsion was heated at 75° C. of the inner temperature by the same reactor as in Example 1. Polymerization was carried out with stirring for 2 hours, 0.1 g of ammonium persulfate dissolved in 10 g of water was added and the reaction was further carried out for 2 hours whereby a polymer emulsion was obtained.

Example 9

The same operation as in Example 8 was carried out except that 10 g of 1-menthol were used instead of limonene in Example 8 to obtain a polymer emulsion.

Example 10

Into a beaker were placed 10 g of limonene, 6 g of EMULGEN 420, 1 g of ethanol and 100 g of water. The resultant mixture was treated with an ultrasonic homogenizer for 10 minutes with stirring whereby a perfume dispersion was prepared. To this perfume dispersion were added 100 g of the polymer emulsion obtained in Example 1 and the reaction was carried out by heating at 40° C. for 4 hours to obtain a polymer emulsion.

Comparative Example 1

To 2.5 g of chitosan (SK-10 manufactured by Koyo Chemical Co., degree of deacetylation: 85–88%, weight average molecular weight: 130000) were added 45 g of water and then 1.0 g of methacrylic acid (equimolar amount to the monosaccharide unit of chitosan) was added thereto and dissolved with stirring at 60° C. to prepare an aqueous solution of chitosan/methacrylic acid.

Then 50 g of n-butyl methacrylate, 1 g of EMULGEN 420, 0.5 g of potassium persulfate and 200 g of deionized water were placed in a reactor made of glass, the inner air was substituted with nitrogen, the inner temperature was made to 80° C. by heating with stirring, the reaction was carried out with stirring for 1 hour, a pre-prepared aqueous solution of chitosan/methacrylic acid was added thereto and polymerization was further carried out for 3 hours whereby a polymer emulsion was obtained.

Comparative Example 2

Into a reactor were placed 100 g of deionized water, 30 g of chitosan (SK-10 manufactured by Koyo Chemical Co., degree of deacetylation: 85–88%, weight average molecular weight: 130000), 15 g of acrylic acid and 400 g of deionized water. The inner temperature was raised up to 70° C., together with substituting of the inner air with nitrogen gas, with stirring. 1 g of potassium persulfate dissolved in 10 g of water was added thereto and then 50 g of n-butyl acrylate were dropped gradually thereinto for 30 minutes. After completion of the dropping, the inner temperature was maintained for 1 hour, then 1 g of sodium bisulfite dissolved in 20 g of water was added and the reaction was carried out by raising the inner temperature up to 80° C. for 2 hours whereby a polymer emulsion was obtained.

Test Example 1

Average particle size and stability of an aqueous dispersion were evaluated by the following method for the chitosan-containing emulsion obtained in each of Examples 1–10 and Comparative Examples 1–2. The result is shown in Table 1.

<Method of Evaluation>

Average Particle Size

Measurement was conducted by means of a light scattering method (using a particle size distribution measuring device LA-910 manufactured by HORIBA) Stability of aqueous dispersion The state (sedimentation of particles, creaming, etc.) after standing left of a chitosan-containing emulsion (solid content: 10% by weight) at 40° C. for 1 month was observed by naked eye.

TABLE 1

| | Composition | | | | | | | | | | Average particle size of polymer emulsions ($\mu$m) | Stability of aqueous dispersion |
|---|---|---|---|---|---|---|---|---|---|---|---|---|
| | Chitosan | Organic acid | | Hydrophobic monomer | | Other component | | Surfactant | | | | |
| Examples | | | | | | | | | | | | |
| 1 | 2.5 g | Methacrylic acid | 1 g | Stearyl methacrylate | 50 g | | | EMULGEN 420 | 5 g | 1.218 | Good |
| 2 | 2.5 g | Methacrylic acid | 1 g | Stearyl methacrylate | 25 g | HNP-9 | 25 g | EMULGEN 420 | 5 g | 1.502 | Good |
| 3 | 2.5 g | Methacrylic acid | 1 g | Lauryl methacrylate | 50 g | | | EMULGEN 420 | 5 g | 1.002 | Good |
| 4 | 2.5 g | Methacrylic acid | 1 g | Stearyl methacrylate | 50 g | | | — | | 1.752 | Good |
| 5 | 2.5 g | Methacrylic acid | 2 g | Stearyl methacrylate | 50 g | N,N-dimethyl acrylamide | 1 g | EMULGEN 420 | 5 g | 1.547 | Good |
| 6 | 2.5 g | Methacrylic acid | 1 g | n-butyl methacrylate | 50 g | Polystyrene latex | 50 g | EMULGEN 420 | 5 g | 2.083 | Good |
| 7 | 2.5 g | Methacrylic acid | 1 g | t-butyl methacrylate | 50 g | Polystyrene latex Isobutyl adipate | 50 g 5 g | EMULGEN 420 | 5 g | 2.323 | Good |
| 8 | 2.5 g | Methacrylic acid | 1 g | Stearyl methacrylate | 50 g | limonene | 10 g | | | 2.064 | Good |
| 9 | 2.5 g | Methacrylic acid | 1 g | Stearyl methacrylate | 50 g | 1-menthol | 10 g | | | 2.279 | Good |

TABLE 1-continued

| | Chitosan | Organic acid | | Hydrophobic monomer | | Other component | Surfactant | | Average particle size of polymer emulsions ($\mu$m) | Stability of aqueous dispersion |
|---|---|---|---|---|---|---|---|---|---|---|
| 10 | 2.5 g | Methacrylic acid | 1 g | Stearyl methacrylate | 50 g | Limonene Ethanol | 10 g 1 g | EMULGEN | 6 g | 2.604 | Good |
| Comparative examples | | | | | | | | | | |
| 1 | 2.5 g | Methacrylic acid | 1 g | n-butyl methacrylate | 50 g | | EMULGEN 420 | 1 g | 308.5 | Particles sedimented |
| 2 | 30 g | Acrylic acid | 15 g | n-butyl acrylate | 50 g | | — | | 80.07 | Particles sedimented |

Test Example 2

Maintenance of Aroma

A Petri dish with the diameter of 5 cm made of glass was applied with an emulsion obtained in Examples 8 and 10 where the perfume was included so as to make the amount of the perfume same or with limonene as Comparative Example. And then, it was placed in an acrylic box in the size of 15 cm x 15 cm x 30 cm and intensity of aroma after elapse of a certain period was organoleptically evaluated according to the following criteria. The result is shown in Table 2. Incidentally, the evaluation was expressed by rounding the average of 10 panelists to the nearest integer.

5: strong, 4: somewhat strong, 3: normal, 2: somewhat weak, 1: weak, 0: no aroma noted.

TABLE 2

| | Intensity of aroma Elapsed period (hour) | | | | |
|---|---|---|---|---|---|
| | 2 | 4 | 8 | 12 | 24 |
| Example 8 | 5 | 5 | 5 | 4 | 4 |
| Example 10 | 5 | 5 | 4 | 4 | 4 |
| Limonene | 5 | 4 | 3 | 1 | 0 |

Test Example 3

Maintenance of Cool Feel

Cotton cloth in the size of 5 cm×5 cm was applied with an emulsion obtained in Example 9 where 1-menthol was included so as to make the amount of 1-menthol same or with an ethanolic solution of 1-menthol as Comparative Example and was attached onto the upper arm. The effect (cool feel) of 1-menthol after elapse of a certain period was organoleptically evaluated according to the following criteria. The result is shown in Table 3. Incidentally, the evaluation was expressed by rounding the average of 10 panelists to the nearest integer.

5: strong, 4: somewhat strong, 3: noted, 2: somewhat weak, 1: weak, 0: not noted.

TABLE 3

| | Intensity of aroma Elapsed period (hour) | | | | |
|---|---|---|---|---|---|
| | 2 | 4 | 8 | 12 | 24 |
| Example 9 | 4 | 4 | 4 | 4 | 3 |
| Limonene | 5 | 4 | 3 | 1 | 0 |

Example 11

Preparation of Coloring Agent Particles A

To 2.5 g of chitosan (SK-10 manufactured by Koyo Chemical Co.; degree of deacetylation: 85–88%, weight average molecular weight: 130000) were added 45 g of water, then 1.0 g of methacrylic acid (an equimolar amount to the monosaccharide unit of chitosan) was added thereto, and the resultant mixture was dissolved with stirring at 60° C. to prepare an aqueous solution of chitosan/methacrylic acid.

Then 13 g of stearyl methacrylate and 0.8 g of lauroyl peroxide were placed in a glass beaker to dissolve. They was added to the above aqueous solution of chitosan/methacrylic acid to which 150 g of deionized water were added. And then the resultant mixture was treated by an ultrasonic homogenizer (manufactured by Nippon Seiki Co. Ltd.) with stirring for 5 minutes to obtain an emulsion of which the average particle size was 1.8 $\mu$m. To this was added a dispersion of Officially Allowed Dye for a medicine, a cleansing agent and a cosmetic 5 g of Blue No. 404, 2 g of EMULGEN 220 and 20 g of deionized water and the resultant mixture was treated by an ultrasonic homogenizer for 1 minute with stirring so as to mix with the monomer liquid particles. The emulsion was transferred to a 1-liter reactor made of glass equipped with stirrer, cooler and nitrogen-introducing pipe, the inner air was substituted with nitrogen and the inner temperature was made 75° C. by heating with stirring. Polymerization was carried out for 2 hours with stirring, then 0.1 g of ammonium persulfate dissolved in 10 g of water was added and the reaction was further carried out for 2 hours to obtain a polymer emulsion of a single distribution of 1.2 $\mu$m including the pigment therein.

The obtained emulsion was freeze-dried and the obtained coloring agent particles were observed by means of SEM or TEM whereby they were confirmed to be spherical having outer shell layer and having the structure of a core-shell type. It was also confirmed that the pigment particles were enclosed in these core-shell particles.

Example 12

Preparation of Coloring Agent Particles B

In Example 11, the amount of methacrylic acid was changed to 0.5 g and 0.8 g of acrylic acid for preparing an aqueous solution of chitosan and stearyl methacrylate was changed to 2-ethylhexyl acrylate whereupon an emulsion was prepared.

Further, Officially Allowed Dye dispersion in Example 11 was changed to 8 g of Red No. 202, 8 g of EMULGEN 220 and 80 g of deionized water and charged whereby a polymer emulsion with a single distribution of 0.5 μm including the pigment therein was obtained.

The obtained coloring agent particles were subjected to the same structural analysis as in Example 11 whereupon the structure of a core-shell type was confirmed. The pigment particles were confirmed to be enclosed in these core-shell particles.

Example 13

A hair rinse having the composition as shown in Table 4 was prepared by a normal process and its appearance, hair-dyeing effect and transfer of color to the skin were evaluated. The result is shown in Table 4 as well.

(Method of Evaluation)

(1) Appearance

Appearance of the hair rinse was evaluated by naked eye according to the following criteria.

○: homogeneous and no problem in terms of appearance

×: aggregation and separation were noted and the appearance of the composition was not homogeneous (2) Hair-dyeing Effect 1 g of a tuft of hair of goat was shampooed and 0.2 g of each hair rinse was applied, uniformly spread by fingers and well rinsed with warm water immediately followed by drying. This was subjected to a colorimetry using a color difference meter CR-300 manufactured by Minolta and the color difference (ΔE) from the original color of hair of the goat was measured and evaluated according to the following criteria. The more the value of ΔE was, the higher the dyeing effect was.

○: ΔE was 40 or more.

Δ: ΔE was 20 or more but less than 40.

×: ΔE was less than 20.

(3) Transfer of the Color to the Skin

To a pig skin in the size of 2 cm×2 cm was applied 0.03 g of a rinse followed by well rinsing with warm water. After being dried, the same colorimetry as in (2) was conducted and the color difference (ΔE) was measured and evaluated according to the following criteria.

○: ΔE was less than 10.

Δ: ΔE was 10 or more but less than 20.

×: ΔE was 20 or more.

TABLE 4

| Component (% by weight) | Products of the present invention | | Products of comparison | | | |
| --- | --- | --- | --- | --- | --- | --- |
|  | 1 | 2 | 1 | 2 | 3 | 4 |
| Stearyl trimethyl ammonium chloride | 1 | 1 | 1 | 1 | 1 | 1 |
| Coloring agent particles A (Example 11) | 5 | — | — | — | — | — |
| Coloring agent particles B (Example 12) | — | 5 | — | — | — | — |
| Blue No. 1 (water-soluble dye) | — | — | 0.5 | — | — | — |
| Blue No. 404 (pigment) | — | — | — | 0.5 | — | — |
| Polymer particles C including the coloring material therein*1 | — | — | — | — | 5 | — |
| Polymer particles D including the coloring material therein*2 | — | — | — | — | — | 5 |
| Polyoxyethylene (4) polyoxypropylene (30) stearyl ether | 1 | 1 | 1 | 1 | 1 | 1 |
| Isostearyl glyceryl ether | 0.5 | 0.5 | 0.5 | 0.5 | 0.5 | 0.5 |
| Hydroxyethyl cellulose | 0.5 | 0.5 | 0.5 | 0.5 | 0.5 | 0.5 |
| Isopropyl myristate | 2 | 2 | 2 | 2 | 2 | 2 |
| Cetanol | 3 | 3 | 3 | 3 | 3 | 3 |
| Propylene glycol | 2 | 2 | 2 | 2 | 2 | 2 |
| Glycerol | 3 | 3 | 3 | 3 | 3 | 3 |
| Perfume | q.s. | q.s. | q.s. | q.s. | q.s. | q.s. |
| Deioned water | Balance | Balance | Balance | Balance | Balance | Balance |
| Appearance | ○ | ○ | ○ | × | × | ○ |
| Hair-dyeing effect | ○ | ○ | × | Δ | ○ | Δ |
| Transfer of color to the skin | ○ | ○ | ○ | × | × | Δ |

*1Polymer of stearyl acrylate containing 10% by weight of Blue No. 404 in inner-part thereof
*2Polymer of chitosan with acrylic acid containing 10% by weight of Blue No. 404 in inner-part thereof It is apparent from the result of Table 4 that all of the products of the present invention selectively colored the hydrophobic surface (hair) with little coloration of the hydrophilic surface (skin). In addition, the products were excellent in stability and in hair-dyeing effect and, furthermore, they did not damage the hair and their feel in actual use was good as well.

Example 14

To 40 g of chitosan (SK-10 manufactured by Koyo Chemical Co., degree of deacetylation: 85–88%, weight average molecular weight: 130000) were added water to make 900 g, and then 120 g of methacrylic acid were added thereto. The resultant mixture was dissolved with stirring at 60° C. to prepare an aqueous solution of chitosan and methacrylic acid. To this were added 3 g of potassium persulfate dissolved in 100 g of deionized water and the resultant mixture was stirred at 25° C. for 5 minutes. To this chitosan solution was added a solution of 1.0% by weight of sorbitan monolaurate in cyclohexane in a ratio of 1:1 by weight. The resultant mixture was made to react at 70° C. for 5 hours and stirred with 1 kg of isopropyl alcohol to separate a solid from liquid. After that, an operation of solid-liquid separation by adding 500 g of isopropyl alcohol thereto was carried out twice followed by drying under reduced pressure at 50° C. to obtain powdery fine particles. 2.5 g of the fine particles were dispersed in 500 ml of water. The resultant dispersion was applied to cotton fiber and the fiber was squeezed until the applied solution became 20% by weight to the cotton fiber and dried whereupon a deodorizing fiber was prepared.

Example 15

Water was added to 20 g of same chitosan as in Example 14 to make 700 g and then 50 g of methacrylic acid and 30 g of acrylic acid were added thereto and dissolved with stirring at 60° C. whereby an aqueous solution of chitosan, methacrylic acid and acrylic acid was prepared. To this were added 3 g of potassium persulfate dissolved in 100 g of deionized water and the resultant mixture was stirred at 25° C. for 5 minutes. This chitosan solution was applied to a cotton fiber, and the fiber was squeezed so that the solid in the applied solution might become 20% by weight to the cotton fiber. After that, it was made to react at 75° C. for 5 hours, washed with 300 g of ethyl alcohol and dried to obtain a deodorizing fiber.

Example 16

Water was added to 50 g of same chitosan as in Example 14 to make 900 g and 100 g of methacrylic acid were added thereto and dissolved with stirring at 60° C. whereby an aqueous solution of chitosan and methacrylic acid was prepared. To this were added 70 g of lauryl methacrylate and 1 g of lauryl peroxide and the resultant mixture was irradiated with ultrasonic wave for 5 minutes to prepare an emulsion. This was made to react at 75° C. for 2 hours, 2 g of potassium persulfate dissolved in 20 g of deionized water were added and the resultant mixture was made to react at 75° C. for 3 hours. After that, a 1N aqueous solution of sodium hydroxide was dropped gradually thereinto to neutralize so that 75% by weight of polymethacrylic acid might be neutralized. This was applied to a cotton fiber, and the fiber was squeezed so that the solid in the applied solution might become 10% by weight to the cotton fiber. After that, dried under reduced pressure at 90° C. for 5 hours to obtain a deodorizing fiber.

Examples 17–20

An emulsion was prepared using monomer compositions as shown in Table 5 and fixed onto the fiber shown in Table 5 to obtain a deodorizing fiber as same operation in Example 16.

Comparative Example 3

Chitosan powder was mechanically disintegrated finely (particle size of disintegrated particles: about 5 μm), applied to a cotton fiber as an aqueous solution and dried as it was to obtain a deodorizing fiber.

Comparative Example 4

The same operation as in Example 16 was carried out except that 75 g of chitosan were dissolved in 25 g of acetic acid and this resultant product was applied to a cotton fiber and dried as same as in Example 16 to obtain a deodorizing fiber.

Deodorant test was carried out for the deodorizing fibers obtained in Examples 14–20 and Comparative Examples 3–4 according to the following method. The result is shown in Table 5.

<Method for the Deodorant Test>

Each 100 ppm of the following 4 types of gas, i.e. acetic acid, ammonia, acetaldehyde and methyl mercaptan, were sealed into a 1-m$^3$ glass container, 1 g of each of the samples shown in Table 1 was placed therein, amount of the gas after 30 minutes was determined by a gas detector pipe and the decreasing value from the initial stage was defined as a deodorizing rate. When the deodorizing rate was 100%, that means all of the gas in the system was deodorized.

TABLE 5

| | Deodorant (% by weight)*1 | | | | | | | | Average |
|---|---|---|---|---|---|---|---|---|---|
| | Component (S) | Starting monomer of component (b)*2 | | | | | | Other component | particle size |
| | Chitosan | MAA | AA | MAA-Na | AA-Na | LMA | SMA | Acetic acid | (μm) |
| Examples | | | | | | | | | |
| 14 | 25 | 75 | | | | | | | 5.0 |
| 15 | 20 | 50 | 30 | | | | | | 3.0 |
| 16 | 22 | 11 | | 34 | | 33 | | | 1.0 |
| 17 | 12 | | | 20 | | 68 | | | 0.8 |
| 18 | 15 | 5 | | 15 | | 65 | | | 2.0 |
| 19 | 30 | | | 20 | | | 50 | | 0.9 |
| 20 | 12 | | | | 20 | | 68 | | 1.2 |
| Comparative examples | | | | | | | | | |
| 3 | 100 | | | | | | | | — |
| 4 | 75 | | | | | | | 25 | — |

TABLE 5-continued

| | Fiber component (% by weight)*1 | | | Deodorizing ratio (%) | | | |
|---|---|---|---|---|---|---|---|
| | Cotton | Nylon | Polyester | Acetic acid | Ammonia | Acetaldehyde | Methyl mercaptan |
| Examples | | | | | | | |
| 14 | 99.9 | | | 60 | 50 | 30 | 40 |
| 15 | 80 | | | 80 | 100 | 60 | 80 |
| 16 | 90 | | | 75 | 90 | 55 | 75 |
| 17 | | 95 | | 85 | 85 | 60 | 80 |
| 18 | | 88 | | 90 | 90 | 65 | 85 |
| 19 | | | 50 | 95 | 80 | 75 | 95 |
| 20 | | 95 | | 70 | 80 | 55 | 70 |
| Comparative examples | | | | | | | |
| 3 | 80 | | | 35 | 10 | 10 | 25 |
| 4 | 80 | | | 20 | 0 | 5 | 15 |

(Notes)
*1Rate of each component in the deodorant
*2MAA: Methacrylic acid
AA: Acrylic acid
MAA-Na: Sodium methacrylate
AA-Na: Sodium acrylate
LMA: Lauryl methacrylate
SMA: Stearyl methacrylate
*3Ratio by weight of the fiber component to the deodorant

What is claimed is:

1. A polymer emulsion comprising polymer particles having core-part and shell-part and having an average particle size of not more than 30 μm;
   wherein the shell-part is composed of chitosan (a) and a polymer (b) of an organic acid having a reactive vinyl group or a salt thereof as constituent components, and
   wherein the core-part is composed of a polymer (c) of a hydrophobic monomer as constituent component.

2. A polymer emulsion comprising polymer particles having core-part and shell-part and having an average particle size of not more than 30 μm;
   wherein the shell-part is composed of chitosan (a) and a polymer (b) of an organic acid having a reactive vinyl group or a salt thereof as constituent components, and
   wherein the core-part is composed of a mixture of a polymer (c) of a hydrophobic monomer and a non-polymerizable hydrophobic substance (d) as constituent component.

3. A process for preparing the polymer emulsion defined in claim 1; which comprises
   emulsifying and dispersing, in water, chitosan (a), an organic acid having a reactive vinyl group or a salt thereof (e), a hydrophobic monomer (f) and an oil-soluble polymerization-initiator (g), to obtain liquid particles of monomers having an average particle size of not more than 10 μm and
   polymerizing the liquid particles, to form the core-part and the shell-part of the polymer particle.

4. A process for preparing the polymer emulsion defined in claim 2; which comprises
   emulsifying and dispersing, in water, chitosan (a), an organic acid having a reactive vinyl group or a salt thereof (e), a hydrophobic monomer (f), a non-polymerizable hydrophobic substance (d) and an oil-soluble polymerization-initiator (g), to obtain liquid particles of monomers having an average particle size of not more than 10 μm and
   polymerizing the liquid particles, to form the core-part and the shell-part of the polymer particle.

5. The process for preparing the polymer emulsion as claimed in claim 3; which comprises
   adding a water-soluble polymerization-initiator (h) during, or after completion of, polymerization of the core-part in the monomer liquid particles and
   polymerizing the shell-part in the monomer liquid particles.

6. A process for preparing the polymer emulsion as defined in claim 1; which comprises
   adding a hydrophobic monomer (f) to polymer particles (i) being miscible with the hydrophobic monomer (f) and having an average particle size of not more than 10 μm, to swell the polymer particles (i),
   further adding thereto an aqueous solution of chitosan (a) and an organic acid having a reactive vinyl group or a salt thereof (e) and
   polymerizing the core-part and the shell-part in the swollen polymer particles thus obtained, in the presence of an oil-soluble polymerization-initiator (g).

7. A process for preparing the polymer emulsion as defined in claim 2; which comprises
   adding a non-polymerizable hydrophobic substance (d) and a hydrophobic monomer (f) to polymer particles (i) being miscible with the hydrophobic monomer (f) and having an average particle size of not more than 10 μm, to swell the polymer particles (i),
   further adding thereto an aqueous solution of chitosan (a) and an organic acid having a reactive vinyl group or a salt thereof (e) and
   polymerizing the core-part and the shell-part in the swollen polymer particles thus obtained, in the presence of an oil-soluble polymerization-initiator (g).

8. A process for preparing the polymer emulsion as defined in claim 1; which comprises
   adding a hydrophobic monomer (f) to polymer particles (i) being miscible with the hydrophobic monomer (f)

and having an average particle size of not more than 10 μm, to swell the polymer particles (i), further adding thereto an aqueous solution of chitosan (a) and an organic acid having a reactive vinyl group or a salt thereof (e) and polymerizing the core-part and the shell-part in the swollen polymer particles thus obtained, in the presence of an oil-soluble polymerization-initiator (g) and a water-soluble polymerization-initiator (h).

9. A process for preparing the polymer emulsion defined in claim 2; which comprises adding a non-polymerizable hydrophobic substance (d) and a hydrophobic monomer (f) to polymer particles (i) being miscible with the hydrophobic monomer (f) and having an average particle size of not more than 10 μm, to swell the polymer particles (i), further adding thereto an aqueous solution of chitosan (a) and an organic acid having a reactive vinyl group or a salt thereof (e) and polymerizing the core-part and the shell-part in the swollen polymer particles thus obtained, in the presence of an oil-soluble polymerization-initiator (g) and a water-soluble polymerization-initiator (h).

* * * * *

UNITED STATES PATENT AND TRADEMARK OFFICE
CERTIFICATE OF CORRECTION

PATENT NO. : 6,252,003 B1
DATED : June 26, 2001
INVENTOR(S) : Kuwahara et al.

Page 1 of 1

It is certified that error appears in the above-identified patent and that said Letters Patent is hereby corrected as shown below:

<u>Title page,</u>
Item [30] Foreign Application Priority Data has been ommited. Item [30] should read as follows:

(30)   Foreign Application Priority Data

Jun. 4, 1998   (JP) ................................. 10-155852

Signed and Sealed this

Twenty-sixth Day of March, 2002

Attest:

JAMES E. ROGAN
*Attesting Officer*   *Director of the United States Patent and Trademark Office*